United States Patent [19]

Wierzbicki

[11] Patent Number: 4,567,196
[45] Date of Patent: Jan. 28, 1986

[54] THIENO [2,3-b] PYRROLE COMPOUNDS AND THEIR USE IN ALLEVIATING PAIN

[75] Inventor: Michel Wierzbicki, Puteaux, France

[73] Assignee: ADIR, S.A.R.L., Neuilly-sur-Seine, France

[21] Appl. No.: 667,909

[22] Filed: Nov. 2, 1984

[30] Foreign Application Priority Data

Nov. 10, 1983 [FR] France ................ 83 17866

[51] Int. Cl.$^4$ ............... C07D 495/06; A61K 31/38
[52] U.S. Cl. ................... 514/422; 548/453
[58] Field of Search ................ 548/453; 514/422

[56] References Cited

FOREIGN PATENT DOCUMENTS 0200740  6/1983  German Democratic Rep. ............... 548/453

Primary Examiner—Glennon H. Hollrah
Assistant Examiner—D. B. Springer
Attorney, Agent, or Firm—Gordon W. Hueschen

[57] ABSTRACT

New thieno [2,3-b] pyrrole compounds of the formula:

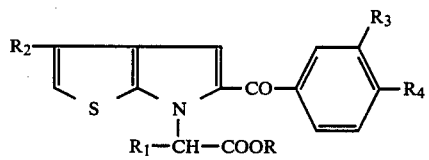

in which:
R is hydrogen, ($C_1$–$C_5$) alkyl, alkali or alkaline earth metals ammnonium or mono- di- or tri-($C_1$–$C_5$) alkylammnonium;
$R_1$ is hydrogen, or ($C_1$–$C_5$) alkyl;
$R_2$ is hydrogen, ($C_1$–$C_5$) alkyl, phenyl or phenyl-($C_1$–$C_5$) alkyl;
$R_3$ and $R_4$, the same or different are each hydrogen, halogen, ($C_1$–$C_5$) alkyl, ($C_1$–$C_5$) alkoxy, or
$R_3$ and $R_4$ together represent: —CH=CH—CH=CH—.

These new compounds may be used as medicines especially in the treatment of acute or chronic pain.

7 Claims, No Drawings

THIENO[2,3-b] PYRROLE COMPOUNDS AND THEIR USE IN ALLEVIATING PAIN

The present invention provides thieno[2,3-b]pyrrole compounds of the general formula I:

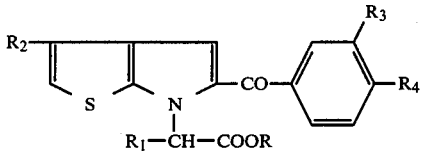

in which:

R is selected from the group consisting of: a hydrogen atom, straight-chain and branched alkyl radicals having from 1 to 5 carbon atoms inclusive, alkali and alkaline earth metals, an ammonium radical, and mono-, di- and tri-alkylammonium radicals in which the and each alkyl groups contain from 1 to 5 carbon atoms inclusive, $R_1$ is selected from the group consisting of: a hydrogen atom and straight-chain and branched alkyl radicals having from 1 to 5 carbon atoms inclusive, $R_2$ is selected from the group consisting of: a hydrogen atom, straight-chain and branched alkyl radicals having from 1 to 5 carbon atoms inclusive, a phenyl radical and phenylalkyl radicals in which the alkyl groups are straight-chain and branched and contain from 1 to 5 carbon atoms inclusive, $R_3$ and $R_4$ which are the same or different, are each selected from the group consisting of: a hydrogen atom, a hydrogen atom, straight-chain and branched alkyl and alkoxy radicals each having from 1 to 5 carbon atoms inclusive, and $R_3$ and $R_4$ together represent a radical of the formula: $-CH=CH-CH=CH-$ in order to form with the phenyl group to which they are bonded a naphthyl group.

The present invention also relates to a process for the preparation of derivatives of the general formula I, characterised in that:

a derivative of the general formula II

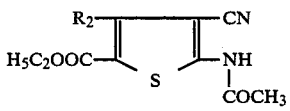

in which $R_2$ has the meaning given above is treated with a derivative of the general formula III

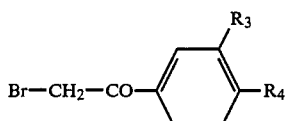

in which $R_3$ and $R_4$ have the meanings given hereinbefore, in the presence of $K_2CO_3$ and acetone to obtain a derivative of the general formula IV

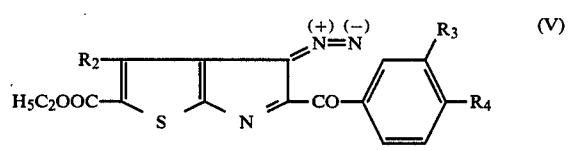

in which $R_2$, $R_3$ and $R_4$ are as defined hereinbefore, which compound IV is treated with $KNO_2$, $HCl/H_2O$ and $CH_3OH$ to obtain a compound of the general formula V

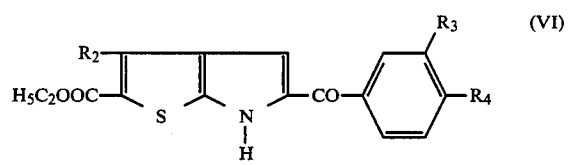

in which $R_2$, $R_3$ and $R_4$ have the meanings given hereinbefore, which compound is dediazotized by means of azabisisobutyronitrile in ethanol to yield a compound of the general formula VI

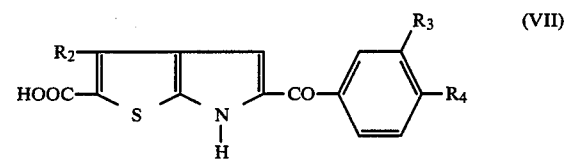

in which $R_2$, $R_3$ and $R_4$ have the meanings given hereinbefore, which compound is treated first of all with $NaOH/H_2O/C_2H_5OH$ and then with $HCl/H_2O$ to yield a compound of the general formula VII

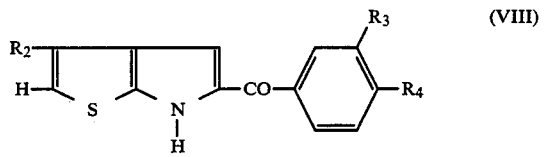

in which $R_2$, $R_3$ and $R_4$ have the meanings given hereinbefore, which compound is heated in the presence of copper and quinoline to obtain a compound of the general formula VIII

in which $R_2$, $R_3$ and $R_4$ have the meanings given hereinbefore, which compound is treated in the presence of $C_2H_5ONa/C_2H_5OH$ with a derivative of the general formula IX

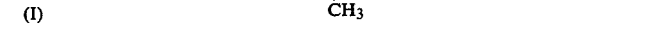

in which $R_1$ has the meaning given hereinbefore and $R'$ has the same meaning as R with the exception of a hydrogen atom, to obtain a derivative of the general formula I'

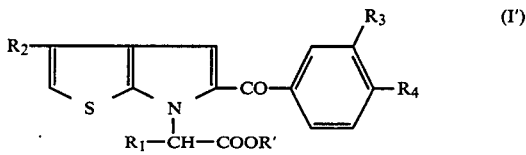 (I')

in which $R'$, $R_1$, $R_2$, $R_3$ and $R_4$ have the meanings given hereinbefore, wich derivative (I') is treated with $NaOH/H_2O/C_2H_5OH$ then with a hydrochloric acid solution to obtain a derivative of the general formula I''

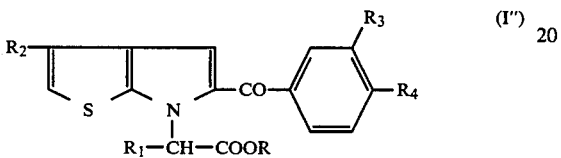 (I'')

in which $R_1$, $R_2$, $R_3$ and $R_4$ have the meanings given hereinbefore.

The aggregate of the derivatives (I') and (I'') forms the total of the derivatives of the general formula I.

The starting materials of the general formula II were prepared in accordance with the method of Gewald K et. al. Chem. Ber. (1966), 99 p. 94 and 2712 from known raw materials.

The compounds of the general formula I have interesting pharmacological properties, especially analgesic properties and, to a lesser degree, anti-inflammatory properties.

Their toxicity is low and their $LD_{50}$ ascertained per os in mice is higher than 1000 mg/kg.

The analgesic activity of the compounds of the invention has been exhibited in particular by the test according to Hendershot, L. C., Forsaith, J. J., J. Pharmacol. Exp. Ther. (1959), 125, 237, relating to abdominal cramps induced by phenylbenzoquinone, and by the test according to Koster, R, Anderson M., de Beer E. S., Fed. Proc. (1959), 18, 412, relating to writhing induced with acetic acid. For each of these tests the average effective dose $ED_{50}$ in the case of the compounds of the invention is between 50 and 200 mg/kg when administered orally to mice.

The pharmacological properties described above and the low toxicity of the compounds of the general formula I permits them to be used therapeutically chiefly in the treatment of acute or chronic pain, especially pain associated with an inflammatory process (rheumatic pain or arthrosis, arthrisis, lumbo-sciatica etc.), traumatic, post-traumatic or post-operative pain, pains in the ORL, stomatological or genito-urinary spheres, and also certain cephalic pains, neuralgias, migraines and cancer pains.

The present invention relates also to pharmaceutical compositions containing as active ingredient a compound of the general formula I mixed or associated with an appropriate pharmaceutical excipient, such as, for example, distilled water, glucose, lactose, starch, talc, ethyl cellulose, magnesium stearate or cocoa butter.

The pharmaceutical compositions obtained in this manner are generally in dosage form and may contain from 25 to 250 mg of active ingredient. They may, for example, be in the form of tablets, dragées, gelatin-coated pills, suppositories, injectable or drinkable solutions or in the form of ointments and, depending upon the case in question, be administered orally, rectally, parenterally or locally at a dosage of from 25 to 250 mg from 1 to 4 times per day.

The following Examples illustrate the invention; unless stated otherwise, the melting points are determined using a Kofler hot plate.

EXAMPLE 1

3-methyl-5-benzoyl-6-carboxymethylthieno[2,3-b]pyrrole

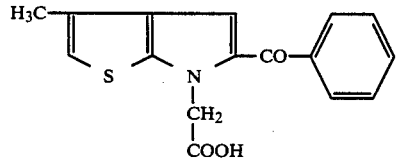

250 g of 2-acetamido-3-cyano-4-methyl-5-ethoxycarbonylthiophene, prepared in accordance with the method of K. Gewald, are refluxed for 24 hours in 1500 ml of acetone with 250 g of α-bromoacetophenone and 220 g of potassium carbonate; the whole is then precipitated in 4000 ml of ice-water. The resulting precipitate is filtered, washed with 1000 ml of an iced mixture of water/ethanol (1/1), then dried and finally washed with 1000 ml of a cold mixture of cyclohexane/benzene (9/1). In this manner 295 g of 2-ethoxycarbonyl-3-methyl-4-amino-5-benzoyl-6-acetylthieno[2,3-b]pyrrole are obtained, m.p.: 188° C.

By the same method, there were obtained:

2-ethoxycarbonyl-3-methyl-4-amino-5 (p.methylbenzoyl)-6-acetyl thieno[2,3-b]pyrrole, M.P.: 198°-199° C.

2-ethoxycarbonyl-3-propyl-4-amino-5-benzoyl-6-acetyl thieno[2,3-b]pyrrole, M.P.: 149° C.;

2-ethoxycarbonyl-3-methyl-4-amino-5 (3,4-dimethoxybenzoyl)-6-acetyl thieno[2,3-b]pyrrole, M.P.: 204° C.;

2-ethoxycarbonyl-3-methyl-4-amino-5-(2-naphthoyl)-6-acetyl thieno[2,3-b]pyrrole M.P.: 220°-221° C.;

2-ethoxycarbonyl-3-methyl-4-amino-5 (p.chlorobenzoyl)-6-acetyl thieno[2,3-b]pyrrole M.P.: 140° C.;

2-ethoxycarbonyl-3-methyl-4-amino-5-(p.methoxybenzoyl)-6-acetyl thieno[2,3-b]pyrrole, M.P.: 201° C.

The 2-ethoxycarbonyl-3-methyl-4-amino-5-benzoyl-6-acetyl thieno[2,3-b]pyrrole, so-obtained is suspended in 2000 ml of methanol, and in succession, portions of 25 ml of HCl (4N) and of 8.5 g of potassium nitrite in 20 ml of $H_2O$ are added thereto until the starting material or its deacetylated analogue has disappeared. The reaction mixture is then filtered, washed with a mixture of water/methanol 1/1 and the product obtained, 2-ethoxycarbonyl-3-methyl-4-diazo-5-benzoyl[4H]-thieno[2,3-b]pyrrole, is used as such in the following process. A recrystallised specimen melts at 180° C.

The product obtained is added to 1500 ml of ethanol and 5 ml of $H_2SO_4$ at 10%, and the whole is refluxed while adding from time to time a catalytic amount of azabisisobutyronitrile (ABIN) and distilling off the acetaldehyde formed. Once the evolution of nitrogen is complete, the whole is cooled, the ethanol is evaporated using a rotary evaporator and the isobutyronitrile formed is sublimed under reduced pressure. In this manner 200 g of 2-ethoxycarbonyl-3-methyl-5-benzoyl-thieno[2,3-b]pyrrole are obtained which can be used as such; a recrystallised specimen melts at 180°–181° C.

By the same method, there were obtained:
2-ethoxycarbonyl-3-methyl-5 (p.methylbenzoyl) thieno[2,3-b]pyrrole, M.P.: 198° C.;
2-ethoxycarbonyl-3-propyl-5-benzoyl thieno[2,3-b]pyrrole, M.P.: 151° C.;
2-ethoxycarbonyl-3-methyl-5-(3,4-dimethoxybenzoyl) thieno[2,3-b]pyrrole, M.P.: 270°–272° C.;
2-ethoxycarbonyl-3-methyl-5-(2-naphthoyl) thieno[2,3-b]pyrrole, M.P.: 189°–190° C.;
2-ethoxycarbonyl-3-methyl-5-(p.chlorobenzoyl) thieno[2,3-b]pyrrole, M.P.: 195° C.;
2-ethoxycarbonyl-3-methyl-5-(p.methoxybenzoyl) thieno[2,3-b]pyrrole, M.P.: 155° C.

The 200 g of 2-ethoxycarbonyl-3-methyl-5-benzoyl thieno[2,3-b]pyrrole, preciously obtained are refluxed in a mixture of 60 g of NaOH, 1500 ml of water and 1500 ml of ethanol until hydrolysis is complete (approximately 15 hours). The ethanol is then distilled, and the mixture is cooled and filtered; the filtrate is acidified to a pH of approximately 3 and filtered. The resulting product is washed with water, then dried and used as such (yield almost quantitative).

The acid so obtained is mixed with 1200 ml of quinoline. 2 g of copper powder are added and the whole is heated; decarboxylation occurs towards 200°–210° C., and the temperature is increased to boiling. The whole is cooled and hydrolysed in a stoichiometric amount of hydrochloric acid (4N) to which ice has been added. The resulting precipitate is filtered, washed with HCl (N) and then recrystallised in ethanol.

In this manner 145 g of 3-methyl-5-benzoylthieno[2,3-b]pyrrole are obtained; M.P.=199° C.

By the same method, there were obtained:
3-methyl-5-(p.methylbenzoyl) thieno[2,3-b]pyrrole, M.P.: 256° C.;
3-propyl-5-benzoyl thieno[2,3-b]pyrrole, M.P.: 155° C.;
3-methyl-5-(3,4-dimethoxy-benzoyl) thieno[2,3-b]pyrrole, M.P.: 191° C.;
3-methyl-5-(2-naphthoyl) thieno[2,3-b]pyrrole M.P.: 179° C.;
3-methyl-5-(p.chlorobenzoyl) thieno[2,3-b]pyrrole M.P.: 233° C.;
3-methyl-5-(p.methoxybenzoyl) thieno[2,3-b]pyrrole, M.P.: 198° C.

The previously obtained 3-methyl-5-benzoyl thieno[2,3-b]pyrrole, suspended in 500 ml of ethanol is added to a sodium ethoxide solution freshly prepared by dissolving 24.6 g of sodium in 500 ml of ethanol, and the whole is agitated for 15 minutes; then 125 g of ethyl bromoacetate are added. The whole is refluxed for 4 hours and then hydrolysed by the addition of 600 ml of sodium hydroxide solution (N). The whole is refluxed for 30 minutes and the ethanol is eliminated by distillation. The cooled solution is then filtered. The filtrate is acidified to a pH of approximately 3, and the precipitate obtained is washed with water and recrystallised in a mixture of benzene and cyclohexane. In this manner 150 g of 3-methyl-5-benzoyl-6-carboxymethylthieno[2,3-b]pyrrole are obtained; m.p.=197° C.

EXAMPLES 2–8

The following derivatives were obtained in accordance with the process described in Example 1:

(2) 3-methyl-5-benzoyl-6-($\alpha$-carboxyethyl)thieno[2,3-b]pyrrole, $\nu$CO: 1620 and 1720 cm$^{-1}$;
(3) 3-methyl-5-(p-methoxybenzoyl)-6-carboxymethyl-thieno[2,3-b]pyrrole, m.p.=144° C.;
(4) 3-methyl-5-(p-chlorobenzoyl)-6-($\alpha$-carboxyethyl)-thieno[2,3-b]pyrrole, m.p.=117°–118° C., m.p. of the corresponding sodium salt >250° C.;
(5) 3-methyl-5-(3,4-dimethoxybenzoyl)-6-($\alpha$-carboxyethyl)thieno[2,3-b]pyrrole, M.P.: 199° C.;
(6) 3-(n.propyl)-5-benzoyl-6-($\alpha$-carboxyethyl) thieno[2,3-b]pyrrole, $\nu$CO: 1610 and 1730 cm$^{-1}$;
(7) 3-methyl-5-(p-methylbenzoyl)-6-($\alpha$-carboxyethyl) thieno[2,3-b]pyrrole, $\nu$CO: 1610 and 1730 cm$^{-1}$;
(8) 3-methyl-5-(2-naphthoyl)-6-($\alpha$-carboxyethyl) thieno[2,3-b]pyrrole, $\nu$CO: 1615 and 1725 cm$^{-1}$. We claim:

1. A compound selected from the group consisting of: thieno[2,3-b]pyrrole compounds of the formula I:

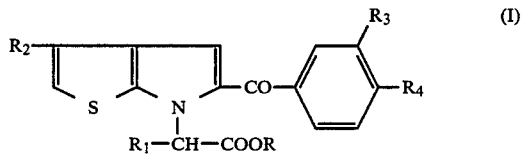

in which
R is selected from the group consisting of hydrogen straight-chain and branched alkyl having from 1 to 5 carbon atoms inclusive, alkali and alkaline-earth metals, ammonium and mono-, di- and tri-alkylammonium in which the and each alkyl group contain from 1 to 5 carbon atoms inclusive,
$R_1$ is selected from the group consisting of hydrogen straight-chain and branched alkyl having from 1 to 5 carbon atoms inclusive,
$R_2$ is selected from the group consisting of hydrogen straight-chain and branched alkyl having from 1 to 5 carbon atoms inclusive, phenyl and phenylalkyl in which the alkyl groups are straight-chain or branched and contain from 1 to 5 carbon atoms inclusive,
$R_3$ and $R_4$, which are the same or different, are each selected from the group consisting of hydrogen, halogen and straight-chain and branched alkyl and alkoxy and each having from 1 to 5 carbon atoms inclusive, and
$R_3$ and $R_4$ together represent a radical of the formula: —CH=CH—CH=CH— in order to form with the phenyl group to which they are bonded a naphthyl group.
2. A compound of claim 1 which is 3-methyl-5-benzoyl-6-carboxymethyl-thieno[2,3-b]pyrrole.
3. A compound of claim 1 which is 3-methyl-5-benzoyl-6-($\alpha$-carboxyethyl)-thieno[2,3-b]pyrrole.
4. A compound of claim 1 which is 3-methyl-5-(p-methoxybenzoyl)-6-carboxy-methylthieno[2,3-b]pyrrole.
5. A compound of claim 1 which is 3-methyl-5-(p-chlorobenzoyl)-6-($\alpha$-carboxyethyl)-thieno[2,3-b]pyrrole.
6. A pharmaceutical composition useful for alleviation of pain containing as active ingredient a compound of claim 1 together with an appropriate excipient.
7. A method for treating a living animal body afflicted with pain comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 4,567,196

DATED : January 28, 1986

INVENTOR(S) : Michel Wierzbicki

It is certified that error appears in the above-identified patent and that said Letters Patent is hereby corrected as shown below:

Title Page [57] ABSTRACT, line 3 after the formula; "ammnonium" should read -- ammonium --

Col. 1, line 22; delete "the and"
Col. 1, line 37; "hydrogen" should read -- halogen --
Col. 3, line 14; "wich" should read -- which --
Col. 3, approx. line 24, (second formula) "$R_1 \cdot - CH - COOR$" should read -- $R_1 - CH - COOH$ --

Col. 6, line 32; delete "the and"

Title Page [57] ABSTRACT, line 4 after the formula; "alkylammnonium" should read -- alkylammonium --

Signed and Sealed this

Seventeenth Day of June 1986

[SEAL]

Attest:

DONALD J. QUIGG

Attesting Officer

Commissioner of Patents and Trademarks